(12) United States Patent
Watanabe (10) Patent No.: US 6,430,988 B1
(45) Date of Patent: Aug. 13, 2002

(54) ULTRASONIC LEAKAGE INSPECTION DEVICE OF NON-PRESSURE TYPE

(75) Inventor: Yuji Watanabe, Mitaka (JP)

(73) Assignee: M.E.C. & Co., Ltd., Tokyo (JP)

( * ) Notice: Subject to any disclaimer, the term of this patent is extended or adjusted under 35 U.S.C. 154(b) by 0 days.

(21) Appl. No.: 09/491,816

(22) Filed: Jan. 26, 2000

(30) Foreign Application Priority Data

Jan. 27, 1999 (JP) .......................................... 11-017930

(51) Int. Cl.⁷ .................... G01M 3/24; G01N 29/00; G01N 29/24
(52) U.S. Cl. .................................. 73/40.5 A; 73/592
(58) Field of Search .............................. 73/40.5 A, 584, 73/592, 598, 600

(56) References Cited

U.S. PATENT DOCUMENTS

| 4,066,095 A | * | 1/1978 | Massa ........................ 73/40.5 A |
| 4,416,145 A | * | 11/1983 | Goodman et al. ........ 73/40.5 A |
| 4,901,576 A | * | 2/1990 | Rademacher ................ 73/592 |
| RE33,977 E | * | 6/1992 | Goodman et al. ........ 73/40.5 A |
| 6,220,098 B1 | * | 4/2001 | Johnson et al. ................ 73/592 |

FOREIGN PATENT DOCUMENTS

FR 2310558 * 1/1977 .............. 73/40.5 A

* cited by examiner

*Primary Examiner*—Daniel S. Larkin
(74) *Attorney, Agent, or Firm*—Hutchins, Wheeler & Dittmar

(57) ABSTRACT

Leakage inspection of items, such as vessels and pipings, is performed using an ultrasonic wave under no pressure with a device of simple structure. The ultrasonic leakage inspection device according to the present invention comprises an ultrasonic wave emitting unit having at least one ultrasonic emitting element for emitting an ultrasonic wave of a predetermined frequency and an ultrasonic detector including an ultrasonic sensor for detecting an ultrasonic wave. For leakage inspection of the items, the ultrasonic emitting unit is put inside the item in a sealed condition so that the ultrasonic wave is emitted uniformly inside the item, and the ultrasonic sensor is moved around the item. Any leakage defects of the item can be detected by sensing any ultrasonic wave leaked therefrom by the ultrasonic sensor.

11 Claims, 7 Drawing Sheets

ULTRASONIC LEAKAGE INSPECTION DEVICE OF NON-PRESSURE TYPE

BACKGROUND OF THE INVENTION

1. Field of the Invention

The present invention relates to an ultrasonic leakage inspection device of non-pressure type which performs leakage inspection of an item like a vessel, such as a fuel tank or a pipe.

2. Description of the Prior Art

For example, various types of closed vessels such as a fuel tank and a drum, are required to be inspected for leakage of a gas or a liquid from inside thereof. Pipes for buildings, facilities, and electric appliances are also required to be inspected for leakage of a gas or a liquid from inside thereof. The leakage inspection of these items has heretofore been carried out by various methods.

Figure 1:
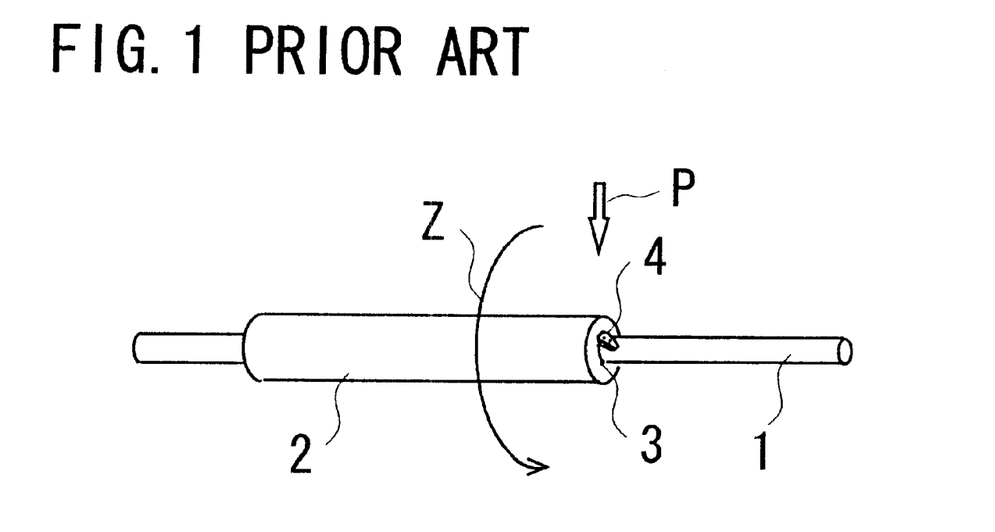
FIG. 1 shows an example of a conventional leakage inspection which is called a bubble type leakage inspection in which air or gas is fed under pressure.

FIG. 1 shows a pipe 1 through which air or a gas flows under pressure and to which an inspection called a bubble type leakage inspection is applied. In the case that the leakage inspection of a connecting portion 3 between the pipe 1 and a joint 2 is done, a viscous liquid is sprayed like an arrow P while the joint 2 is rotated in the direction of an arrow Z, and the leakage is inspected on the basis of a forming condition of a bubble 4.

Figure 2:
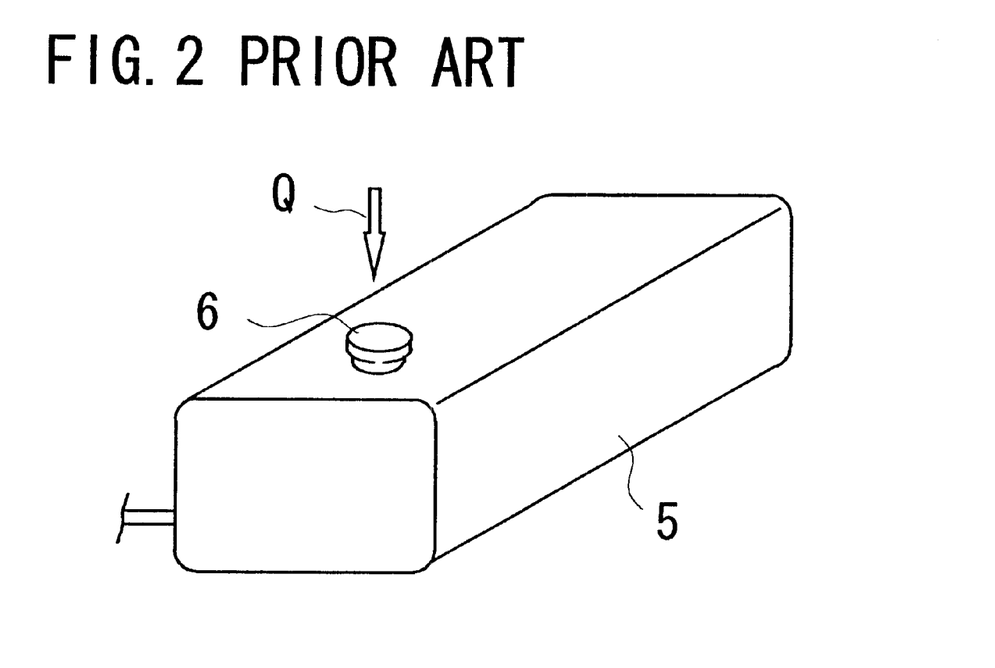
FIG. 2 shows another example of a conventional leakage inspection which is applied to a fuel tank.

FIG. 2 shows a fuel tank 5 to which the same bubble type leakage inspection is applied. In the case that the leakage inspection of the fuel tank 5 is done, a lid 6 of an injection port is removed and air or a nitrogen gas is fed into the fuel tank 5 under pressure like an arrow Q through the injection port, and the lid 6 is then put thereon. Afterward, a viscous liquid is sprayed onto a portion to be inspected, such as a joint, and then the leakage is inspected on the basis of a condition of a bubble appearing on the portion.

In another inspection method which is called a water immersion type leakage inspection, air or nitrogen gas is injected into the inside of an item to be inspected, and the item is then hermetically sealed. Then, the item is immersed in water, and the leakage is then inspected on the basis of a condition of a bubble.

In a further inspection method which is called a helium type leakage inspection, the inside of an item to be inspected is evacuated, and the leakage inspection is then done by use of helium gas.

However, the above-mentioned conventional leakage inspection methods have the following problems.

The bubble type leakage inspection in which a viscous liquid is sprayed onto a portion to be inspected is laborious for the inspection, and after the inspection, a troublesome operation, such as wiping, is also required. In addition, such visual inspection is liable to miss defective portions of the items; and there is a problem that it is difficult to detect a very small leak. Moreover, in the case of the leakage inspection for piping, when portions to be inspected are complicatedly positioned among a plurality of pipes, there is a fear that it is impossible to do the spraying onto such complicated places. Additionally, when the portions to be inspected are concealed and so cannot be visually confirmed, there is a fear that the leakage inspection is impossible.

Besides, in the water immersion type leakage inspection in which air or nitrogen gas is fed under pressure into the item to be inspected, a troublesome working, such as drying, is required after the inspection, and so this type of inspection is laborious. Additionally, there is a problem that it is difficult to detect a very small leak.

Moreover, in the helium type leakage inspection in which the inside of the item to be inspected is evacuated and the leakage inspection is performed by use of helium gas, an inspection device is extremely expensive, and helium gas used for the inspection is also extremely expensive. In addition, a laborious and troublesome working must be performed.

SUMMARY OF THE INVENTION

The present invention has been made in consideration of the above-mentioned facts, and it is an object of the present invention to provide an innovative ultrasonic leakage inspection device of non-pressure type having a simplified structure which more easily detects the leakage of items, such as a vessel or a pipe.

DETAILED DESCRIPTION OF THE PREFERRED EMBODIMENTS

The present invention will now be described below with reference to embodiments thereof.

Figure 3:
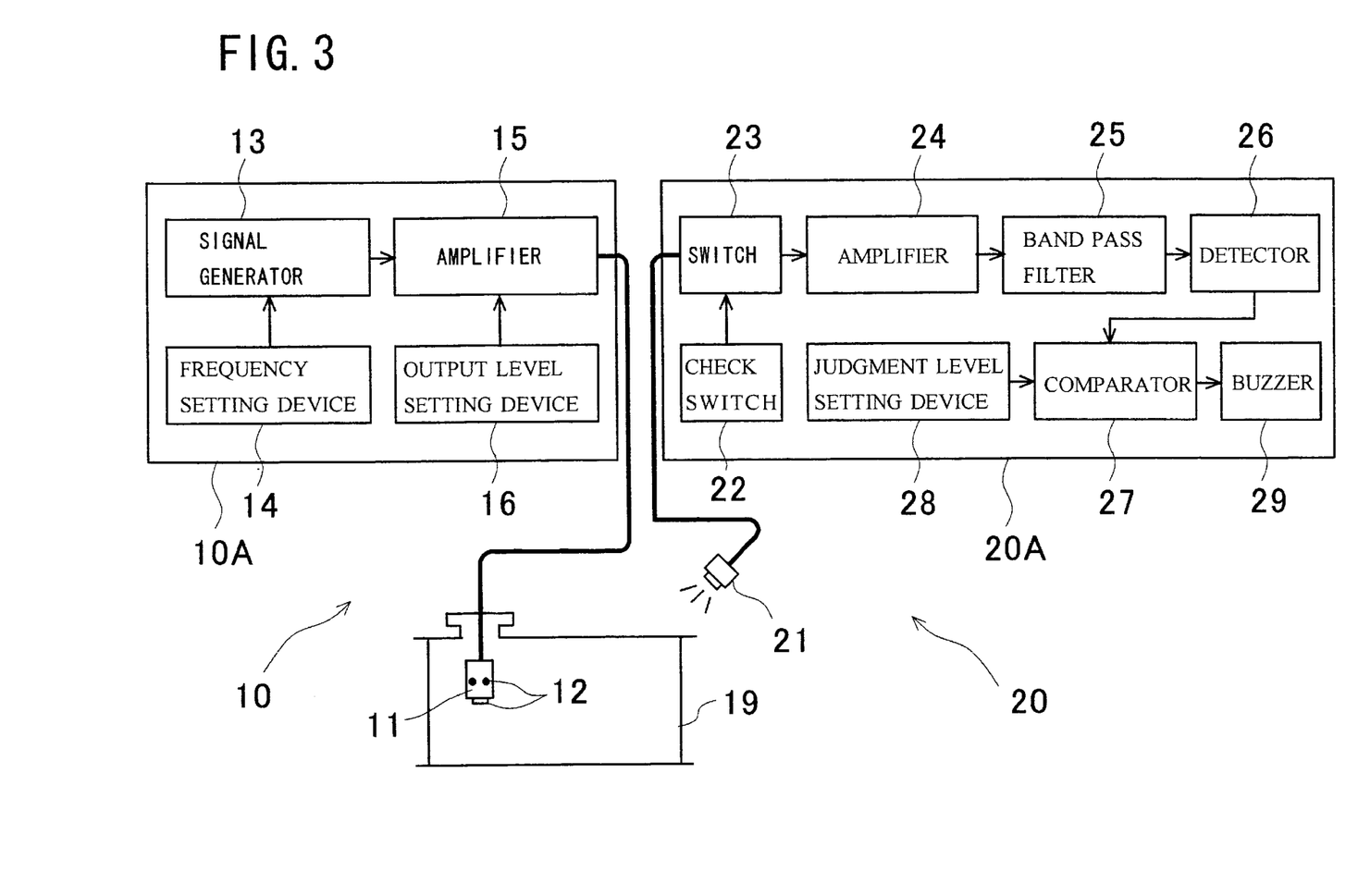
FIG. 3 shows a whole constitutional view of an ultrasonic leakage inspection device of non-pressure type according to the present invention.

FIG. 3 shows a whole constitutional view of an ultrasonic leakage inspection device of non-pressure type according to the present invention.

The ultrasonic leakage inspection device comprises an ultrasonic transmitter 10 which emits an ultrasonic wave inside an item 19 to be inspected, which is shown in FIG. 3 as a fuel tank for a vehicle by way of example, and an ultrasonic detector 20 which detects an ultrasonic wave that may leak out of the item 19 or the fuel tank.

The ultrasonic transmitter 10 is constituted of an ultrasonic emitting unit 11 which is disposed inside the item 19 to emit an ultrasonic wave, and an ultrasonic transmitting circuit unit 10A which outputs a predetermined signal to the ultrasonic emitting unit 11. The ultrasonic transmitting circuit unit 10A gives a predetermined signal to the ultrasonic emitting unit 11 which emits an ultrasonic wave. The ultrasonic transmitting circuit unit 10A is constituted of a signal generator 13 which generates a signal having a predetermined frequency (40 KHz), a frequency setting device 14 which changes a frequency of the signal generated by the signal generator 13, an amplifier 15 which amplifies the signal from the signal generator 13, and an output level setting device 16 which varies the amplification of the amplifier 15 and can set the output level of the amplifier 15.

The ultrasonic emitting unit 11 disposed inside the fuel tank 19 outputs an ultrasonic wave according to the output from the ultrasonic transmitting circuit unit 10A. The ultrasonic emitting unit 11 is usually provided with a plurality of the ultrasonic transmitting elements 12 so as to uniformly emit an ultrasonic wave inside of the fuel tank 19 and may be provided with at least one or more ultrasonic transmitting elements according to the shape and size of the item to be inspected.

The ultrasonic detector 20 comprises an ultrasonic sensor 21 which detects an ultrasonic wave leaked from the fuel tank 19 and an ultrasonic detection circuit unit 20A. The ultrasonic sensor 21 which is directed to the fuel tank 19 is connected to a switch 23 to which a check switch 22 is connected and the switch 23 is connected to a band-pass filter 25 via an amplifier 24. The band-pass filter 25 passes through a frequency in a predetermined narrow band, and passes through only the signal of an ultrasonic wave having a specific frequency leaked from the fuel tank 19.

The band-pass filter 25 is connected to a detector 26 which outputs a signal having a level depending upon the amplitude of an ultrasonic signal as detected. The detector 26 is connected to a comparator 27 where the output of the detector 26 is compared with the preset level of a judgment level setting device 28 and a leakage signal is outputted to a connecting buzzer 29 indicating that there is leakage if the output level of the detector 26 is higher than the preset level.

Operation of the ultrasonic leakage detection device shown in FIG. 1 will be described.

The ultrasonic emitting unit 11 is disposed inside the fuel tank 19 as an item to be inspected in the sealed condition and emits ultrasonic waves from a plurality of the ultrasonic transmitting elements 12 mounted on the ultrasonic output unit 11 on the basis of a signal having a predetermined frequency generated by the ultrasonic transmitting circuit unit 10A. The ultrasonic wave emitted from the ultrasonic transmitting element 12 leaks outside at a leakage portion if the fuel tank 19 has such leakage portion.

The ultrasonic wave which will leak at the leakage portion of the fuel tank 19 can be detected while the ultrasonic sensor 21 is moved around the fuel tank 19. Upon operation of the check switch 22, the detection signal of the ultrasonic sensor 21 passes through the switch 23 and is amplified by the amplifier 24 and is then supplied to the band-pass filter 25. The band-pass filter 25 passes through only the frequency bands of 37 to 43 KHz in the vicinity of the ultrasonic wave (40 KHz) emitted from the ultrasonic transmitting element 12. The comparator 27 compares the output of detector 26 with the preset level of the judgment level setting device 28 and outputs a leakage signal which actuates a buzzer 29 indicating that there is leakage if the output of the detector 26 is higher than the preset level. Thus, the leakage inspection of the fuel tank 19 is completed. In FIG. 1, the leakage is indicated by the buzzer 29, but detection results may also be displayed or recorded in a digital way.

Leakage inspection can be performed for more than one item in the same manner. It is to be understood that the frequency to be used for the leakage inspection can vary within the range of 20 to 60 KHz.

If desired, the frequency of the ultrasonic wave emitted from the ultrasonic transmitting element 12 can be changed according to the size, shape, and leakage conditions of the item 19 to be inspected by a knob (not shown) provided in the frequency setting device 14. Further, if the output of the ultrasonic wave emitted from the ultrasonic transmitting element 12 needs to be adjusted according to the size, shape, and leakage conditions of the item to be inspected 19, then the output level of the amplifier 15 can be adjusted by a knob (not shown) provided in association with the output level setting device 16.

As described above, the ultrasonic leakage inspection device of non-pressure type can detect the leakage of a vessel or a pipe exceedingly easily without inspection works requiring extensive labor, such as press-fit of air or nitrogen gas, and without using expensive equipment. Further, use of an ultrasonic wave for the detection of leakage is effective in detecting very small leaks with good precision. In addition, high accuracy of reproducibility of leakage inspection can also be expected and the press-fitting work of air or nitrogen gas is not required, which results in improved safety. Furthermore, position of the leakage can accurately be detected by moving the ultrasonic sensor in close relation to an item to be inspected.

Moreover, an ultrasonic wave can evenly and uniformly be generated inside the item to be inspected and the leakage can accurately be detected by disposing the ultrasonic emitting unit 11 inside the item, so that the leakage can be detected properly.

Figure 4:
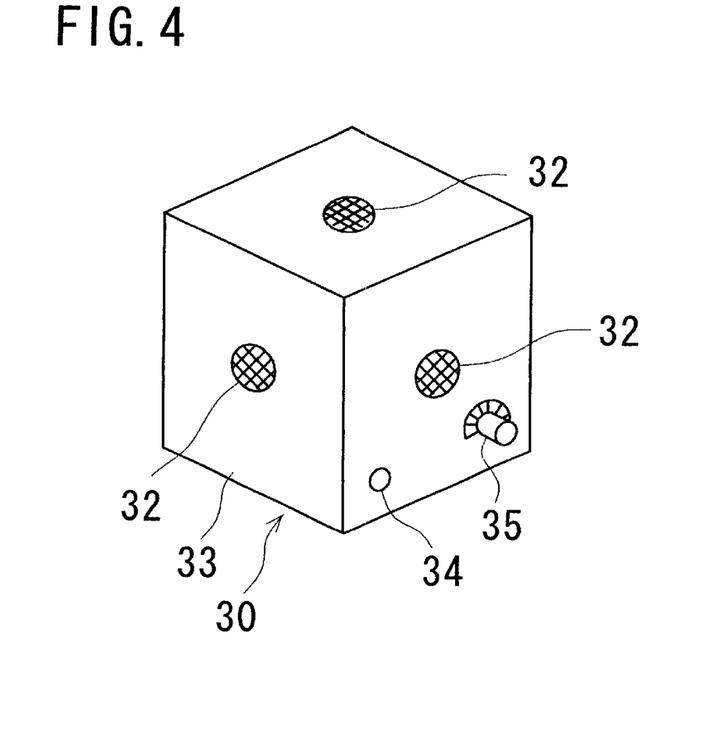
FIG. 4 shows a perspective view of an ultrasonic transmitter of the ultrasonic leakage inspection device according to the present invention which is intended to be arranged in a vessel as an item to be inspected.

FIG. 4 shows a perspective view of an ultrasonic transmitter 30 which is appropriate to detect leakage of a vessel as an item to be inspected. The ultrasonic transmitter 30 is composed of the ultrasonic transmitting circuit unit 10A (see FIG. 1) and ultrasonic transmitting elements 32 integrally arranged in a housing 33 which is of a size of 90 mm (W)×90 mm (D)×90 mm (H), and is placed in the item 19 to be inspected for leakage. The ultrasonic transmitting circuit unit 10A is arranged inside the housing 33 and the ultrasonic transmitting elements 32 are arranged on the outer surface of the housing 33, respectively. A knob 35 which is intended to regulate an ultrasonic output and to function as a power switch and a power lamp 34 for a battery installed inside the housing 33 are provided on the front surface thereof. The frequency of the signal generated from the transmitter 13 can be changed by the knob (not shown) provided on the rear surface of the housing 33. The ultrasonic transmitter 30 is functionally the same as the ultrasonic transmitter 10 and the housing 33 may take various shapes, such as a cylindrical shape or a box-type shape.

Figure 5:
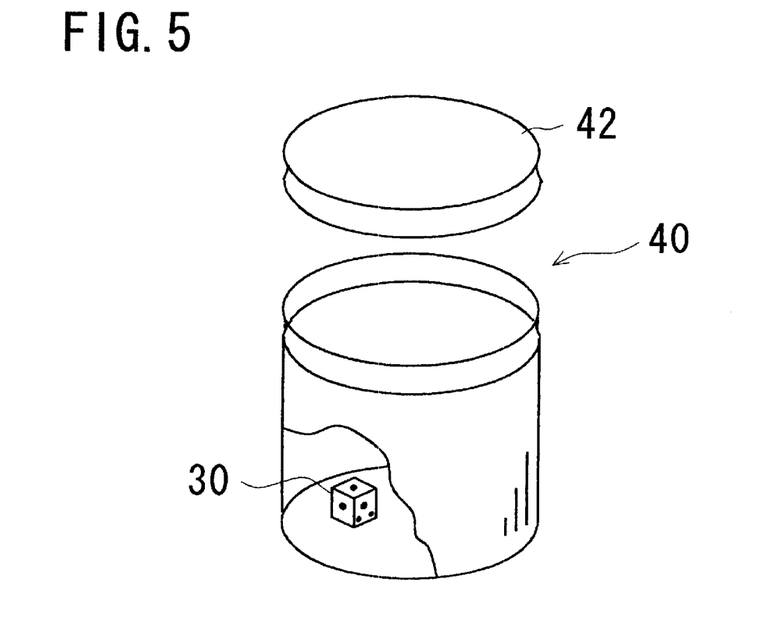
FIG. 5 shows a perspective view of an embodiment of the present invention in which the leakage inspection of an oil reservoir can is performed using the ultrasonic transmitter shown in FIG. 4.

FIG. 5 shows how the leakage inspection is performed for an oil reservoir 40 using the ultrasonic transmitter 30 shown in FIG. 4. When the leakage inspection is performed, a lid 42 is removed, and the ultrasonic transmitter 30 with a power switch on is put in the oil reservoir 40 and the lid 42 is then put thereon. Afterward, the ultrasonic sensor 21 (see FIG. 1) is moved closely to the oil reservoir 40 to detect the leakage of an ultrasonic wave therefrom.

The ultrasonic transmitter 30 is suitable for the leakage inspection of vessels, such as an oil reservoir, whose lid and capacity are rather large. However, the ultrasonic transmitter 30 may also be widely applied to, for example, the leakage inspection of a refrigerator and a room of a vehicle.

As described above, the ultrasonic transmitter 30 can easily be put in the vessels, so that the leakage can easily be detected with simple working. In particular, the inspection technique with the ultrasonic transmitter 30 is suitable for the leakage inspection for vessels having large lids and large capacity, such as an oil reservoir.

Figure 6:
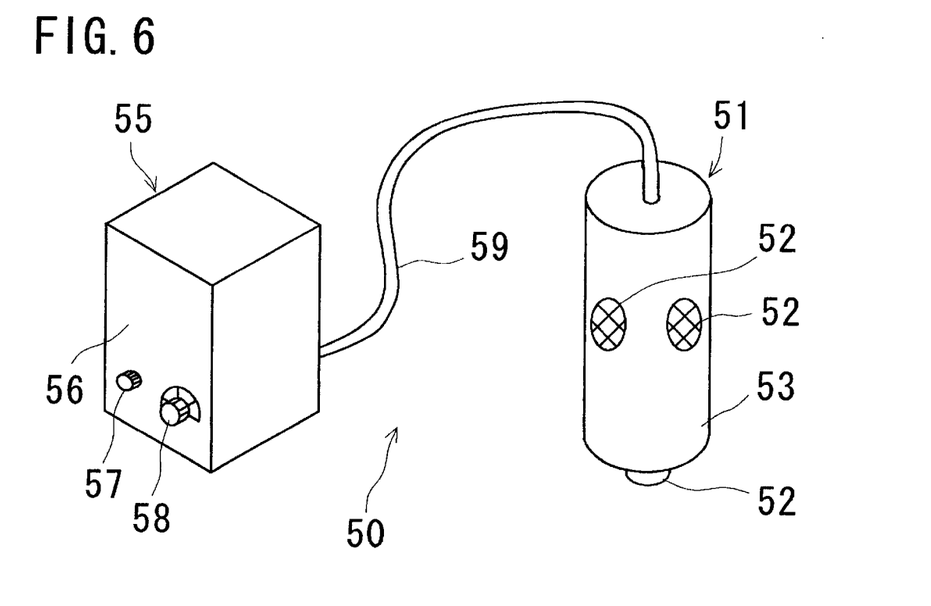
FIG. 6 shows a perspective view of another ultrasonic transmitter for use in leakage inspection of a vessel according to the present invention.

FIG. 6 is a perspective view of an ultrasonic transmitter 50 for use in leakage inspection for a vessel. The ultrasonic transmitter 50 is constituted of an ultrasonic emitting unit 51 and an ultrasonic transmitting circuit unit 55. The ultrasonic emitting unit 51 is put into an item to be inspected for leakage. The ultrasonic emitting unit 51 is constituted of a cylindrical housing 53 of, for example, 20 mm in diameter× 90 mm in height, and a plurality of ultrasonic transmitting elements 52 mounted on the outer surface of the cylindrical housing 53. The ultrasonic transmitting circuit unit 55 includes the ultrasonic transmitting circuit unit 10A and a battery in the housing 56 of 60 mm in width×60 mm in diameter×70 mm in height. On the front surface of the housing 56, there is provided a knob 58 serving an ultrasonic level regulator and a power switch, and a power lamp 57. The ultrasonic transmitting circuit unit 55 is connected to the ultrasonic emitting unit 51 via a signal cable 59. The frequency of a signal from the signal generator 13 can be changed by the knob (not shown) arranged on the rear surface of the housing 56. The ultrasonic transmitter 50 functions in the same manner as the ultrasonic transmitter 10.

Figure 7:
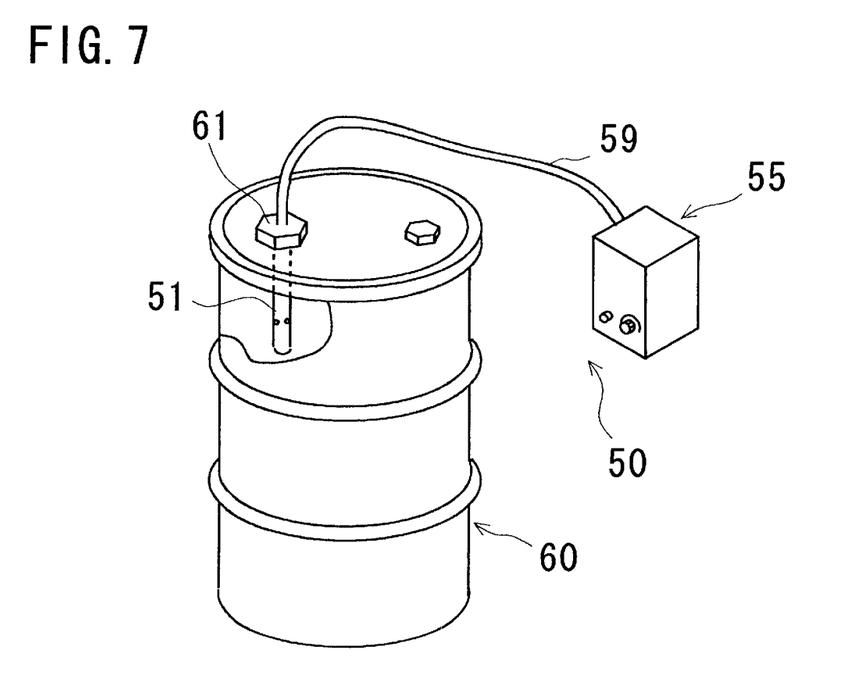
FIG. 7 shows a perspective view of another embodiment of the present invention in which the leakage inspection of a drum can be performed using the ultrasonic transmitter shown in FIG. 6.

FIG. 7 shows how the leakage inspection is performed for a drum can 60 using the ultrasonic transmitter 50 shown in FIG. 6. The drum can 60 has a cap 61 for an injection port on a top plate and the ultrasonic emitting unit 51 is attached inside the cap 61 in advance. A signal cable 59 is connected from the cap 61 to the ultrasonic transmitting circuit unit 55. When starting the leakage inspection for the drum can 60, the cap 61 is removed, the ultrasonic emitting unit 51 is put therein and the cap 61 is closed so that the inside of the drum can 60 is in the sealed state.

The leakage inspection is performed for the drum can 60 by energizing the ultrasonic transmitting circuit unit 55 so that an ultrasonic wave is emitted inside the drum can 60 by the ultrasonic emitting unit 51 while moving the ultrasonic sensor 21 (see FIG. 1) around the drum can 60.

The ultrasonic transmitter 50 can easily be put in vessels with relatively small lids or injection ports. In consequence, an ultrasonic wave can evenly be emitted in the vessels so that leakage can easily be detected.

In the embodiment shown in FIG. 6, the ultrasonic transmitter 50 separately includes the ultrasonic emitting unit 51 with the ultrasonic transmitting circuit unit 10A and a power supply (a batter or an AC adapter), and the ultrasonic transmitting circuit unit 55. However, the ultrasonic transmitting circuit unit 10A and the battery can be incorporated into the ultrasonic emitting unit 51, and such integral unit can be attached to the cap 61 to facilitate the inspection working.

Figure 8:
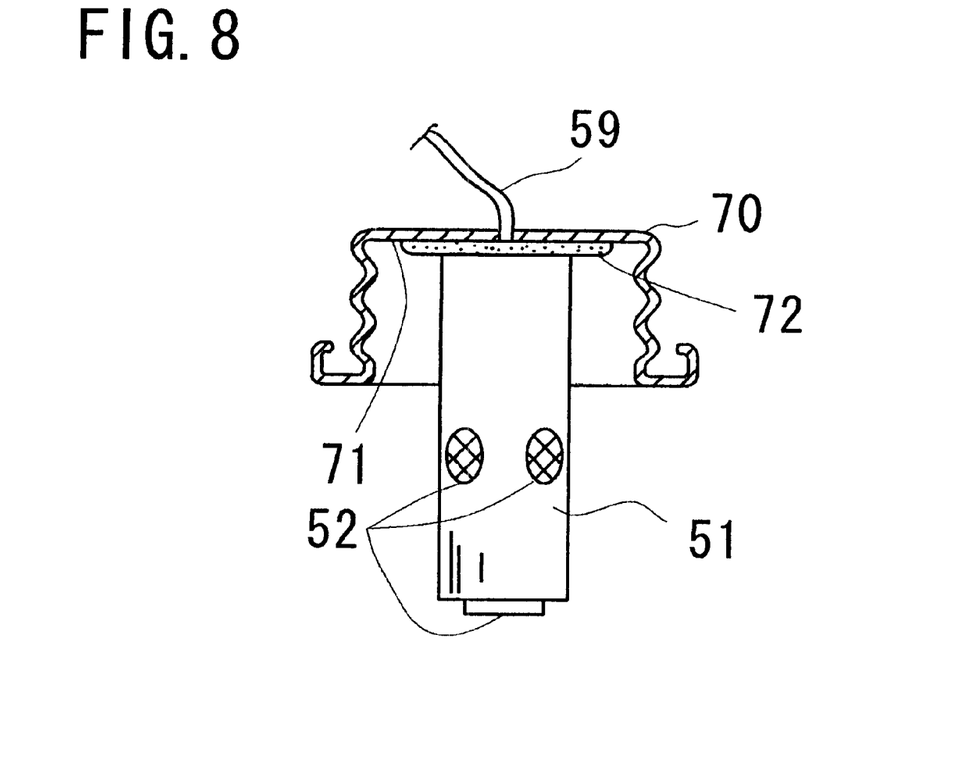
FIG. 8 shows a partially cut side view of the third embodiment of the present invention in which an ultrasonic emitting unit is attached to the lid of a vessel to be inspected.

FIG. 8 shows the ultrasonic emitting unit 51 attached to a lid 70 of a vessel. The ultrasonic emitting unit 51 is fixed to an inner surface 71 of the lid 70, and is sealed with a sealing material 72 from the inner surface 71. A signal cable 59 is connected to the ultrasonic transmitting circuit unit 55 (not shown) through the lid 70. Attachment of the ultrasonic emitting unit 51 is not limited to the lids of vessels, but it may be attached to the vessels themselves. Size of the ultrasonic emitting unit 51 can optionally be adjusted in accordance with the size and shape of the vessel to be inspected, and any desired number of ultrasonic transmitting elements 52 can be mounted on the side and the bottom of the ultrasonic emitting unit 51.

Further, the ultrasonic emitting unit 51 may be suspended from the lid 70 and can be disposed inside the vessel by attaching it to the lid or the cap of the vessel.

Figure 9:
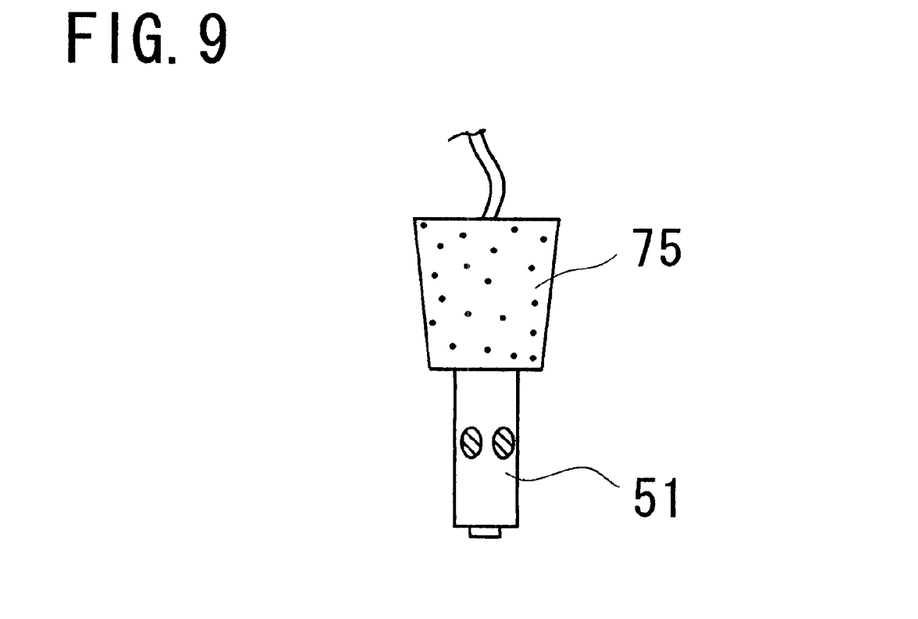
FIG. 9 shows a side elevation view of the ultrasonic output unit attached to an adapter made of an elastic material.

FIG. 9 shows a side elevation view of the ultrasonic emitting unit 51 attached to an adapter 75 of an elastic material. The adapter 75 made of the elastic material can be attached on the vessel only by pushing instead of twisting, which can further curtail a preparation work of leakage inspection.

When attachment of the ultrasonic emitting unit 51 to the vessel, as shown in FIG. 6 and FIG. 7, is employed, an appropriate number of ultrasonic transmitting elements 52 can be arranged at the appropriate positions on the vessel, so that an ultrasonic wave can be evenly emitted inside the vessel.

Figure 10:
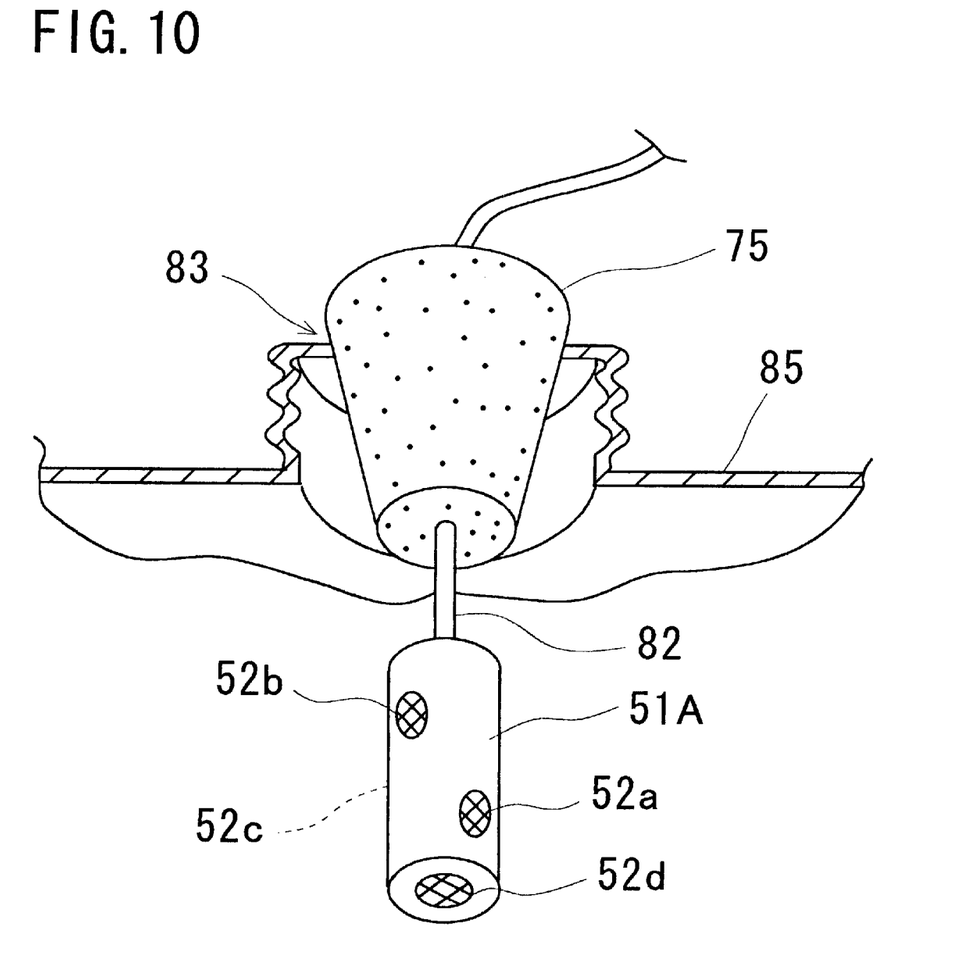
FIG. 10 shows a perspective view of the ultrasonic emitting unit attached with the adapter to an injection port such as lid or cap of a vessel to be inspected.

FIG. 10 shows an ultrasonic emitting unit 51A attached with an adapter 75 to an injection port 83 of the vessel 85 to be inspected. The ultrasonic emitting unit 51A as shown is provided with three ultrasonic transmitting elements 52a, 52b and 52c on the circumferential surface of a cylindrical housing at equidistant positions of 120 degrees in a circumferential direction thereof and one ultrasonic transmitting element 52d on the bottom of the housing. The ultrasonic emitting unit 51A is hanging from the adapter 75 via a signal cable 82, which is drawn out through the adapter 75 and then connected to the ultrasonic transmitting circuit unit 55 (see FIG. 4). The hanging position of the ultrasonic emitting unit 51A can appropriately be adjusted by changing the length of the signal cable 82 depending upon the size and the shape of the vessel to be inspected. Besides, the number of the ultrasonic transmitting elements can be decided for the successful leakage inspection in accordance with the shape and size of the item to be inspected.

Further, the ultrasonic emitting unit 51A can either be fixed to the adapter 75 or be fixed to or hung on the inner surface of the lids or caps. The adapter 75 made of an elastic material, such as silicone rubber, can closely be attached on the injection port 83 of the vessel 85.

The ultrasonic emitting unit 51A can easily be attached inside the vessel in an exceedingly short time only by pushing it without requiring any other working, such as twisting, and emits an ultrasonic wave uniformly and evenly inside the vessel with the ultrasonic transmitting elements 52a, 52b, 52c, and 52d arranged on the circumferential surface and bottom of the vessel. Therefore, the detection of leakage can accurately be performed.

The leakage inspection for the vessels with the ultrasonic emitting unit 51 or 51A may widely be applied to, for example, an extinguisher and a fuel tank.

Figure 11A:
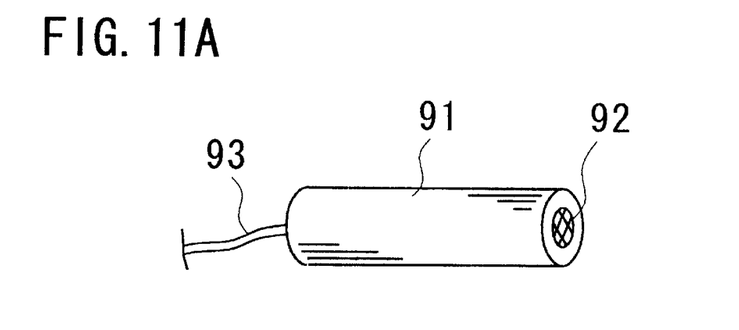
FIG. 11A is a perspective view of an ultrasonic emitting unit for a pipe.
Figure 11B:
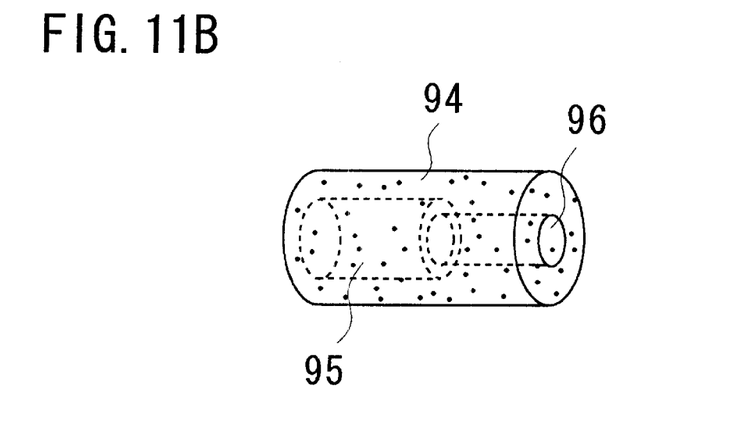
FIG. 11B shows a perspective view of an adapter connected to the ultrasonic emitting unit.

FIG. 11A shows an ultrasonic emitting unit 91 for a pipe and FIG. 11B shows an adapter 94 for use with the ultrasonic emitting unit 91. The ultrasonic emitting unit 91 shown in FIG. 11A is provided with an ultrasonic transmitting element 92 on the side of a cylindrical housing and a signal cable 93 is connected to the ultrasonic transmitting circuit unit 10A (see FIG. 1). The number of ultrasonic transmitting element 92 arranged on the ultrasonic emitting unit 91 may be increased depending upon a diameter thereof.

Figure 12:
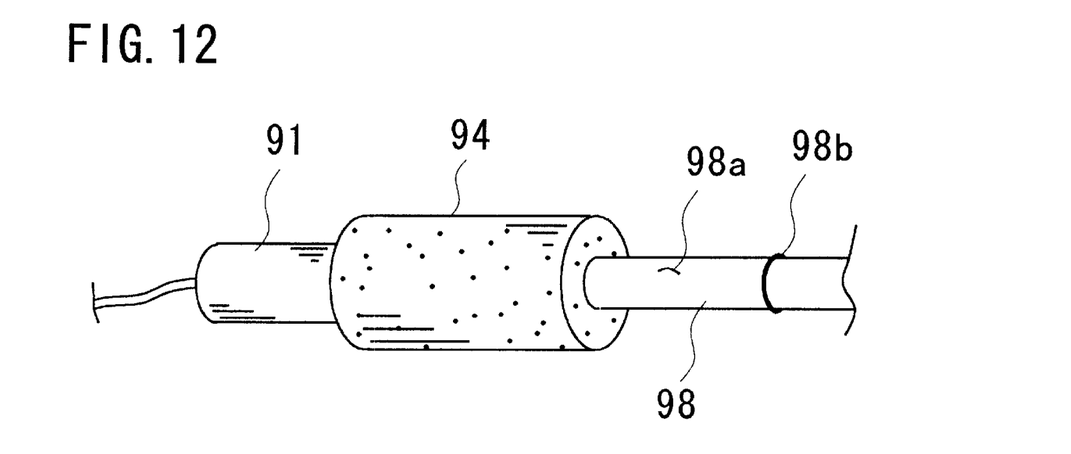
FIG. 12 is a perspective view of the adapter shown in FIG. 11B to which the ultrasonic emitting unit and the pipe to be inspected are connected.

The adapter 94 shown in FIG. 11B is provided with a fitting hole 95 in which the ultrasonic emitting unit 91 is fitted, and another fitting hole 96 communicating with the fitting hole 95 in which a pipe 98 to be inspected is fitted, as shown in FIG. 12. Since the adapter 94 is made of an elastic material, such as silicone rubber, the ultrasonic emitting unit 91 can closely be attached to the pipe 98, and the diameters of the fitting holes 95 and 96 can be decided in compliance with the shape and size of the pipe 98.

FIG. 12 is a perspective view of the ultrasonic emitting unit 91 coupled to the pipe 98 through the adapter 94. The leakage inspection for the pipe 98 can be performed by emitting an ultrasonic wave inside the pipe 98 via the adapter 94 by the ultrasonic emitting unit 91 and by detecting the leakage of the ultrasonic wave from a scratch 98a or a joint 98b on the pipe 98.

The leakage inspection for the pipes with the ultrasonic emitting unit 91 and the adapter 94 can widely apply to welded portions of a heat exchanger for a refrigerator, conditioners, and shock absorbers for a vehicle, for example.

In the ultrasonic emitting unit 91 for the pipe shown in FIG. 11A, the ultrasonic transmitting circuit unit 10A and a power supply (a battery or an AC adapter) are separately installed, but may be incorporated in the ultrasonic emitting unit 91.

The leakage inspection for the pipe with the combination of the ultrasonic emitting unit 91 and the adapter 94 is effective, because an ultrasonic wave is uniformly being emitted inside the pipe and ultra minute leakage can be easily detected with good accuracy.

Table 1 represents results of the test for comparison conducted on leakage inspection for samples of pipes prepared for this purpose. The leakage inspection for comparison was conducted with respect to the conventional water immersion type leakage inspection to which air having an internal pressure of 1.5 MPA applies, conventional helium type leakage inspection, and the ultrasonic leakage inspection of non-pressure type according to the invention. In the helium type leakage inspection, leakage is detected in units of pascal/second/m³ as leakage inspection unit and the result of leakage of sample No. 4 is shown in terms of a least leakage diameter of 0.046 μm. The ultrasonic leakage inspection of nonpressure type was of course successful in leakage detection with respect to sample No. 4. In the water immersion type leakage inspection, open bubbles were detected on samples Nos. 3 and 5, but no leakage could not be confirmed on the remaining samples. In the ultrasonic leakage inspection according to the invention, a leakage diameter can be detected on the basis of a level of a leaked ultrasonic wave.

Because it has been proven from the test results of Table 1 that the ultrasonic leakage inspection of non-pressure type is extremely superior to the water immersion type leakage inspection and is substantially the same or superior to the helium type leakage inspection because the test has proven that as least leakage diameter as 0.01 μm could be detected by the leakage detection of the invention. Accordingly, not only the leakage caused by scratch and on welded portions, but also even very little leakage caused by a bubble generated inside aluminum products and castings can be detected.

TABLE 1

| Sample | Water Immersion Type Leakage Inspection (1.5 MPA) | Helium Type Leakage Inspection | Ultrasonic Non-Pressure Type Leakage Inspection |
| --- | --- | --- | --- |
| No. 1 | Not confirmed | 2.0 μm | Detected |
| No. 2 | Not confirmed | 0.1 μm | Detected |
| No. 3 | Open bubble | 1.0 μm | Detected |
| No. 4 | Not confirmed | 0.046 μm | Detected |
| No. 5 | Open bubble | Not Inspected because of measurement being possible | Detected |

What is claimed is:

1. An ultrasonic leakage inspection device of non-pressure type comprising an ultrasonic transmitter for emitting an ultrasonic wave inside an item to be inspected, and an ultrasonic detector for detecting the ultrasonic wave which is leaked from said item, wherein said ultrasonic transmitter comprises an ultrasonic emitting unit provided with at least one ultrasonic transmitting element disposed on a cylindrical housing and an ultrasonic transmitting circuit unit for generating a predetermined signal to said ultrasonic emitting unit, said ultrasonic emitting unit being disposed inside said item to be inspected when leakage inspection is performed, said ultrasonic emitting unit being fixed to or hung from an adapter made of an elastic material.

2. The ultrasonic leakage inspection device according to claim 1, wherein said ultrasonic transmitter further includes a battery for a power supply, and wherein said at least one ultrasonic transmitting element, said circuit unit, and said battery for said power supply are incorporated in a housing.

3. The ultrasonic leakage inspection device according to claim 1, wherein said ultrasonic emitting unit includes at least three ultrasonic transmitting elements arranged on a circumferential surface of said cylindrical housing and at least one ultrasonic transmitting element arranged on a side of said cylindrical housing.

4. The ultrasonic leakage inspection device according to claim 1, wherein said ultrasonic emitting unit integrally accommodates said ultrasonic transmitting circuit unit and a battery.

5. The ultrasonic leakage inspection device according to claim 1, wherein said ultrasonic emitting unit is fixed to or hung from the inside surface of a lid or a cap detachably mounted on said item.

6. An ultrasonic leakage inspection device of non-pressure type comprising an ultrasonic transmitter for emitting an ultrasonic wave inside an item to be inspected, and an ultrasonic detector for detecting the ultrasonic wave which is leaked from said item, wherein said ultrasonic transmitter comprises an ultrasonic emitting unit in which at least one ultrasonic transmitting element is provided on the side of a cylindrical housing, and an adapter made of an elastic material in one end of which said ultrasonic emitting unit is inserted and in the other end of which said item is inserted in communication with said ultrasonic emitting unit.

7. The ultrasonic leakage inspection device according to claim 6, wherein said ultrasonic emitting unit is disposed inside said item to be inspected when leakage inspection is performed.

8. The ultrasonic leakage inspection device according to claim 6, wherein said ultrasonic transmitter includes an ultrasonic transmitting circuit unit for generating a predetermined signal to said at least one ultrasonic transmitting element, and a battery for a power supply, and wherein said at least one ultrasonic transmitting element, said circuit unit, and said battery for said power supply are incorporated in a housing.

9. The leakage inspection device according to claim 6, wherein said ultrasonic transmitter includes at least three ultrasonic transmitting elements arranged on a circumferential surface of said cylindrical housing and at least one ultrasonic transmitting element arranged on a side of said cylindrical housing.

10. The ultrasonic leakage inspection device according to claim 6, wherein said ultrasonic emitting unit integrally accommodates an ultrasonic transmitting circuit unit and a battery.

11. The ultrasonic leakage inspection device according to claim 6, wherein said ultrasonic emitting unit is fixed to or hung from the inside surface of a lid or a cap detachably mounted on said item.

* * * * *